United States Patent
Vij et al.

(10) Patent No.: US 9,217,064 B2
(45) Date of Patent: Dec. 22, 2015

(54) THERMOSETTING RESINS WITH ENHANCED CURE CHARACTERISTICS CONTAINING ORGANOFUNCTIONAL SILANE MOIETIES

(71) Applicant: The United States of America as Represented by the Secretary of the Air Force, Washington, DC (US)

(72) Inventors: Vandana Vij, Palmdale, CA (US); Andrew Guenthner, Lancaster, CA (US); Timothy Haddad, Lancaster, CA (US); Joseph Mabry, Lancaster, CA (US)

(73) Assignee: THE UNITED STATES OF AMERICA, AS REPRESENTED BY THE SECRETARY OF THE AIR FORCE, Washington, DC (US)

( * ) Notice: Subject to any disclaimer, the term of this patent is extended or adjusted under 35 U.S.C. 154(b) by 0 days.

(21) Appl. No.: 13/748,730

(22) Filed: Jan. 24, 2013

(65) Prior Publication Data

US 2014/0206812 A1  Jul. 24, 2014

(51) Int. Cl.
*C07F 7/10* (2006.01)
*C08G 77/00* (2006.01)
*C07F 7/08* (2006.01)

(52) U.S. Cl.
CPC .............. *C08G 77/80* (2013.01); *C07F 7/0818* (2013.01); *C07F 7/10* (2013.01); *C07F 7/0809* (2013.01)

(58) Field of Classification Search
CPC ....... C07G 7/10; C07G 7/0818; C07G 7/0809
See application file for complete search history.

(56) References Cited

U.S. PATENT DOCUMENTS

| | | | |
|---|---|---|---|
| 2,687,424 A * | 8/1954 | Sommer | 556/416 |
| 3,382,279 A * | 5/1968 | Niederprum et al. | 556/403 |
| 3,465,017 A * | 9/1969 | Coutant | 556/489 |
| 4,709,008 A | 11/1987 | Shimp | |
| 4,774,028 A * | 9/1988 | Imai et al. | 552/505 |
| 4,841,084 A * | 6/1989 | Corriu et al. | 556/464 |
| 5,258,534 A * | 11/1993 | Larson et al. | 556/415 |
| 5,283,348 A * | 2/1994 | Bank | 556/415 |
| 5,284,968 A | 2/1994 | Craig, Jr. | |
| 5,629,394 A * | 5/1997 | Cheradame et al. | 526/219.2 |
| 5,912,377 A | 6/1999 | Hall et al. | |
| 6,057,402 A | 5/2000 | Zhou et al. | |
| 6,217,943 B1 * | 4/2001 | Hall et al. | 427/387 |
| 6,489,380 B1 | 12/2002 | Zhou et al. | |
| 6,716,919 B2 | 4/2004 | Lichtenhan et al. | |
| 6,767,930 B1 | 7/2004 | Svejda | |
| 6,770,724 B1 | 8/2004 | Lichtenhan | |
| 6,844,379 B2 | 1/2005 | Zhou et al. | |
| 7,053,167 B2 | 5/2006 | Ito | |
| 7,193,015 B1 | 3/2007 | Mabry et al. | |
| 7,291,747 B2 | 11/2007 | Oikawa | |
| 7,332,822 B2 | 2/2008 | Basheer | |
| 7,790,841 B1 | 9/2010 | Yandek et al. | |
| 7,897,667 B2 | 3/2011 | Mabry et al. | |
| 8,058,380 B1 | 11/2011 | Vij et al. | |
| 8,276,664 B2 | 10/2012 | Gupta | |
| 8,557,329 B2 | 10/2013 | Dai et al. | |
| 8,565,892 B2 | 10/2013 | Nayfach-Battilana | |
| 8,580,027 B1 | 11/2013 | Campos et al. | |
| 8,741,432 B1 | 6/2014 | Campos et al. | |
| 2001/0016616 A1 | 8/2001 | Yeager et al. | |
| 2005/0009982 A1 | 1/2005 | Inagaki et al. | |
| 2005/0076560 A1 * | 4/2005 | Wiley et al. | 44/320 |
| 2006/0194068 A1 | 8/2006 | Katoh et al. | |
| 2007/0173657 A1 * | 7/2007 | Chen et al. | 556/413 |
| 2008/0199805 A1 | 8/2008 | Rushkin | |
| 2009/0069508 A1 | 3/2009 | Poe | |
| 2009/0176097 A1 | 7/2009 | Brown et al. | |
| 2010/0063244 A1 | 3/2010 | Poe | |
| 2010/0068168 A1 | 3/2010 | Song | |
| 2010/0098761 A1 | 4/2010 | Song | |
| 2010/0159011 A1 | 6/2010 | Lian | |
| 2010/0280561 A1 | 11/2010 | Song | |
| 2012/0000853 A1 | 1/2012 | Tuteja | |
| 2012/0015191 A1 | 1/2012 | Treadway | |
| 2012/0190532 A1 | 7/2012 | Celiker et al. | |
| 2012/0214269 A1 * | 8/2012 | Harding | 438/46 |

OTHER PUBLICATIONS

English abstract, CN 102659827, Sep. 2012.*
J. T. Reams et al., "Effect of chemical structure and network formation on physical properties of di(cyanate ester) thermosets," ACS Appl. Mater. Interfaces, vol. 4 (2012) 527-535.
D. A. Shimp and S. J. Sing, "Moisture effects and their control in the curing of polycyanate resins," ACS PMSE Prepr. vol. 66 (1992) 504-505.
D. A. Shimp et al., "Cyanate esters—a new family of high temperature thermosetting resins," High Temp. Polym. and Their Uses (1989) 127-140.
A. J. Guenthner et al., "A new silicon-containing bis(cyanate) ester resin with improved thermal oxidation and moisture resistance," Macromol., vol. 39 (2006) 6046-6053.

(Continued)

*Primary Examiner* — Margaret Moore
(74) *Attorney, Agent, or Firm* — AFMCLO/JAZ; James P. Carey

(57) ABSTRACT

A reactive, non-hydrolyzable silane. The silane comprises a quaternary silicon atom and first and second terminal groups. Each of the first and second terminal groups is chemically bonded to the quaternary silicon atom and is selected from a group consisting of cyanate ester, epoxide, episulfide, acrylate, alkene, styrenic, maleimide, phthalonitrile, acetylene, aryl ethynylene, benzoxazine, anthracene, aniline, trifluorovinyl ether, and perfluorocyclobutyl.

14 Claims, 6 Drawing Sheets

(56) References Cited

OTHER PUBLICATIONS

A. J. Guenthner et al., "Cure characteristics of tricyanate ester high-temperature composite resins," Presentation, SAMPE 2011 Int'l Techn. Conf. (2011). 22 pages total.

A. J. Guenthner et al., "Synthesis, cure kinetics, and physical properties of a new tricyanate ester with enhanced molecular flexibility," Polymer, vol. 52 (2011) 3933-3942.

A. J. Guenthner et al., "New insights into structure-property relationships in thermosetting polymers from studies of cocured polycyanurate networks," Macromol., vol. 45 (2011) 211-220.

J. N. Hay with Hamerton, I (Ed.), "Processing and cure schedules for cyanate ester resins: cure catalysis and cure rheology," In Chemistry and Technology of Cyanate Ester Resins, published by Blackie Academic (Boca Raton) (1994) 155-170.

M. E. Wright, "The synthesis of new silane based bis(cyanate) ester monomers for use in high performance composite resins," Polymer Preprints vol. 45 (2004) 294, 2 pages total.

E. M. Maya et al., "Oligodimethylsiloxane linked cyanate ester resins," Macromol., vol. 35 (2002) 460-466.

B. Yameen et al., "Polycyanurate thermoset networks with high thermal, mechanical, and hydrolytic stability based on liquid multifunctional cyanate ester monomers with bisphenol A and AF units," Macromol. Chem. Phys., vol. 209 (2008) 1673-1685.

J. V. Crivello and J. L. Lee, "The synthesis, characterization, and photoinitiated cationic polymerization of silicon-containing epoxy resins," J. Polym. Sci. Part A: Polym. Chem., vol. 28 (1990) 479-503.

V. P. McConnell, "Resins for the hot zone, part 2: BMIs, Ces, benzoxazines and phthalonitriles," High Performance Composites, Aug. 18, 2009 (available at http://www.compositesworld.com/articles/resins-for-the-hot-zone-part-ii-bmis-ces-benzoxazines-and-phthalonitriles, accessed on Dec. 17, 2012) 6 pages total.

V. Marella, "Investigation on the hydrolysis of polyphenolic cyanate esters using Near-IR spectroscopy," Thesis submitted to the Faculty of Drexel University (2008) 102 total.

A. J. Guenthner et al., "Supplementary Content: Synthesis, cure kinetics, and physical properties of a new tricyanate ester with enhanced molecular flexibility," Polymer, vol. 52 (2011) 20 pages total.

V. P. McConnell, "Resins for the hot zone, part 1: polyimids," High Performance Composites, Jun. 19, 2009 (available at http://www.compositesworld.com/articles/resins-for-the-hot-zone-part-i-polyimides, accessed on Dec. 17, 2012) 6 pages total.

A. J. Guenthner et al., "Supporting Information: New insights into structure-property relationships in thermosetting polymers from studies of cocured polycyanurate networks," Macromol., vol. 45 (2011) 71 pages total.

O. Georjon and J. Galy, "Effects of crosslink density on mechanical properties of high glass transition temperature polycyanurate networks," J. Appl. Polym. Sci., vol. 65 (1998) 2471-2479.

United States Patent and Trademark Office, Final Office Action in U.S. Appl. No. 14/013,600, mailed Dec. 4, 2014, 5 pages total.

F. J. Feher et al., "A new route to heterosilsesquioxane frameworks," Angew. Chem., Int. Ed. 37 (1998) 2663-2667.

F. J. Feher et al., "A new route to incompletely-condensed silsesquioxanes: acid-mediated cleavage and rearrangement of (c-C6H11)6Si6O9 to C2-[(c-C6H11)6Si6O8X2]," Chem. Commun. (1999) 1705-1706.

F. J. Feher et al., "A new route to incompletely-condensed silsesquioxanes: base-mediated cleavage of polyhedral oligosilsesquioxanes," Chem. Commun. (1999) 2309-2310.

P.D. Lickiss and F. Rataboul, "Chapter 1: Fully condensed polyhedral oligosilsesquioxanes (POSS): From synthesis to application," Adv. Organomet. Chem. vol. 57 (2008) 1-116.

F. J. Feher, "Controlled cleavage of R8Si8O12 frameworks: a revolutionary new method for manufacturing precursors to hybrid inorganic-organic materials," Chem. Commun. (1998) 399-400.

A. Tuteja et al., "Designing superoleophobic surfaces," Science. vol. 318 (2007) 1618-1622.

S. H. Phillips et al., "Developments in nanoscience: polyhedral oligomeric silsesquioxane (POSS)-polymers," Current Opinion in Solid State and Materials Science. vol. 8 (2004) 21-29.

W. Choi et al., "Fabrics with tunable oleophobicity," Adv. Mater. vol. 21 (2009) 2190-2195.

S. T. Iacono et al., "Facile synthesis of hydrophobic fluoroalkyl functionalized silsesquioxane nanostructures," Chem. Commun. (2007) 4992-4994.

J. M. Mabry et al., "Fluorinated polyhedral oliomeric silsesquioxanes (F-POSS)," Angew. Chem., Int. Ed. vol. 47 (2008) 4137-4140.

S. S. Chhatre et al., "Fluoroalkylated silicon-containing surfaces—estimation of solid-surface energy," Appl. Mater. Interfaces. vol. 2 (2010) 3544-3554.

E. G. Shockey et al., "Functionalized polyhedral oligosilsesquioxane (POSS) macromers: new graftable POSS hydride, POSS α-olefin, POSS epoxy, and POSS chlorosilane macromers and POSS-siloxane triblocks," Appl. Organomet. Chem. vol. 13 (1999) 311-327.

R. Duchateau, "Incompletely condensed silsesquioxanes: versatile tools in developing silica-supported olefin polymerization catalysts," Chem. Rev. vol. 102 (2002) 3525-3542.

C. Ohde et al., "Oxovandaium (IV) silsesquioxane complexes," Inorg. Chem. vol. 49 (2010) 2479-2485.

K. Pielichowski et al., "Polyhedral oligomeric silsesquioxane (POSS)-containing nanohybrid polymers," J. Adv. Polym. Sci. vol. 201 (2006) 225-296.

F. J. Feher et al., "Practical methods for synthesizing four incompletely condense silsesquioxanes from a single R8Si8O12 framework," Chem. Commun. (1998) 1279-1280.

A. Tuteja et al., "Robust omniphobic surfaces," PNAS. vol. 105 (2008) 18200-18205.

R. H. Baney et al., "Silsesquioxanes," Chem. Rev. vol. 95 (1995) 1409-1431.

F. J. Feher et al., "Synthesis and structural characterization of a remarkably stable, anionic, incompletely condensed silsesquioxane framework," Chem. Commun. (1997) 829-830.

H. Liu et al., "A spectroscopic investigation of incompletely condensed polyhedral oligomeric silisesquioxanes (POSS-mono-ol, POSS-diol and POSS-triol): hydrogen-bonded interaction and host-guest complex," J. Organomet. Chem. vol. 693 (2008) 1301-1308.

T. W. Dijkstra et al., "Silsesquioxane models for geminal silica surface silanol sites. A spectroscopic investigation of different types of silanols," J. Am. Chem. Soc. vol. 124 (2002) 9856-9864.

S. T. Iacono et al., "Preparation of composite fluoropolymers with enhanced dewetting using fluorinated silsesquioxanes as drop-in modifiers," J. Mater. Chem. vol. 20 (2010) 2979-2984.

F. J. Feher et al., "Facile framework cleavage reactions of a completely condensed silsesquioxane framework," J. Am. Chem. Soc. vol. 119 (1997) 11323-11324.

F. J. Feher et al., "Reactions of incompletely-condensed silsequioxanes with pentamethylantimony: a new synthesis of metallasilsesquioxanes with important implications for the chemistry of silica surfaces," J. Am. Chem. Soc. vol. 114 (1992) 3859-3866.

F. J. Feher and T. L. Tajima, "Synthesis of a molybdenum-containing silsesquioxane which rapidly catalyzes the metathesis of olefins," J. Am. Chem. Soc. vol. 116 (1994) 2145-2146.

F. J. Feher et al., "Silsesquioxanes as models for silica surfaces," J. Am. Chem. Soc. vol. 111 (1989) 1741-1748.

H. M. Cho et al., "A Mo(VI) alkylidyne complex with polyhedral oligomeric silsesquioxane ligands: homogeneous analogue of a silica-supported alkyne metathesis catalyst," J. Am. Chem. Soc. vol. 128 (2006) 14742-14743.

J. D. Lichtenhan et al., "Linear hybrid polymer building blocks: methacrylate-functionalized polyhedral oligomeric silsesquioxane monomers and polymers," Macromol. vol. 28 (1995) 8435-8437.

T. S. Haddad and J. D. Lichtenhan, "Hybrid organic-inorganic thermoplastics: styryl-based polyhedral oligomeric silsesquioxane polymers," Macromol. vol. 29 (1996) 7302-7304.

K. Koh et al., "Precision synthesis of a fluorinated polyhedral oligomeric silsesquioxane-terminated polymer and surface characterization of its blend film with poly(methyl methacrylate)," Macromol. vol. 38 (2005) 1264-1270.

E. Lucenti et al., "Synthesis and characterization of osmium-containing silsesquioxanes: high-yield routes to {Os3(CO)10(μ-H)[μ-

(56) References Cited

OTHER PUBLICATIONS

O)Si7O10(c-C6H11)7]} and the new clusters {Os3(CO)10(μ-H)[μ-O)Si7O9(OH)2(c-C6H11)7]}, {[Os3(CO)10(μ-H)]2[μ-O)2Si7O9(OH)(c-C6H11)7}, {Os3(CO)10(μ-H)[μ-O)Si8O11(OH)(c-C6H11)8]}, and {[Os3(CO)10(μ-H)]2(μ-O)2Si8O11(c-C6H11)8}," Organomet. vol. 26 (2006) 75-82.

K. Wada et al., "Synthesis and catalytic activity of group 4 metallocene containing silsesquioxanes bearing functionalized silyl groups," Organomet. vol. 23 (2004) 5824-5832.

K. Ohno et al., "Living radical polymerization by polyhedral oligomeric silsesquioxane-holding initiators; precision synthesis of tadpole-shaped organic/inorganic hybrid polymers," Macromol. vol. 37 (2004) 8517-8522.

S. T. Iacono et al, "Synthesis, characterization, and surface morphology of pendant polyhedral oligomeric silsesquioxane perfluorocyclobutyl aryl ether copolymers," Macromol. vol. 40 (2007) 9517-9522.

T. Haddad et al, "Polyhedral Oligomeric Silsequioxane (POSS)-Styrene Macromers" Organomet. vol. 11 (2001) 155-164.

R. Duchateau et al, "Silica-Grafted Diethylzinc and a Silsesquioxane-Based Zinc Alkyl Complex as Catalysts for the Alternating Oxirane-Carbon Dioxide Copolymerization" Organomet. vol. 26 (2007) 4204-4211.

Iacono et al., "Synthesis, characterization, and properties of chain terminated polyhedral oligomeric silsesquioxane-functionalized perfluorcyclobutyl aryl ether copolymers," Polymer, vol. 28 (2007) 4637-4645.

Fina et al., "POSS-based hybrids by melt/reactive blending," J. Mater. Chem., vol. 20 (2010) 9297-9305.

Iyer et al., "Thermal and mechanical properties of blended polyimide and amine-functionalized poly(orthosiloxane) composites," J. Appl. Polym. Sci., vol. 108 (2008) 2691-2699.

Moore et al., "Asymmetric aryl polyhedral oligomeric silsesquioxanes (ArPOSS) with enhanced solubility," J. Organomet. Chem., vol. 696 (2011) 2676-2680.

Rosenberg et al., "Preparation of some arylchlorosilanes with arylmagnesium chlorides," J. Organomet. Chem., vol. 22 (1957) 1606-1607.

Wright et al., "Chemical modification of fluorinated polyimides: new thermally curing hybrid polymers with POSS," Macromol., vol. 39 (2006) 4710-4718.

Braunecker et al., "Controlled/living radical polymerizations: features, developments, and perspectives," Prog. Polym. Sci., vol. 52 (2007) 98-146.

Cheng et al., "Phosphonium-containing ABA triblock copolymers: controlled free radical polymerization of phosphonium ionic liquids," Macromol., vol. 44 (2011) 6609-6617.

Destarac, "On the critical role of RAFT agent design in reversible addition-fragmentation chain transfer (RAFT) polymerization," Polym. Rev., vol. 51 (2011) 163-187.

Girard et al., "Direct synthesis of vinylidene fluoride-based amphiphilic diblock copolymers by RAFT/MADIX polymerization," ACS Macro Lett., vol. 1 (2012) 270-274.

Goto et al., "Mechanism and kinetics of RAFT-based living radical polymerizations of styrene and methyl methacrylate," Macromol., vol. 34 (2001) 402-408.

Gregory et al., "Complex polymer architectures via RAFT polymerization: from fundamental process to extending the scope using clink chemistry and nature's building blocks," Prog. Polym. Sci., vol. 37 (2012) 38-105.

Isemura et al., "Dichloropentafluoropropane as solvents for size exclusion chromatography," J. Chromatog. A., vol. 1026 (2004) 109-116.

Lu et al., "L-proline functionalized polymers prepared by RAFT polymerization and their assemblies as supported organocatalysts," Macromol., vol. 44 (2011) 7233-7241.

Mayadunne et al., "Living radical polymerization with reversible addition-fragmentation chain transfer (RAFT polymerization) using dithiocarbamates as chain transfer agents," Macromol., vol. 32 (1999) 6977-6080.

McCormick et al., "Aqueous RAFT polymerization: recent developments in synthesis of functional water-soluble (co) polymers with controlled structures," Acc. Chem. Res., vol. 37 (2004) 312-325.

Moad et al., "Toward living radical polymerization," Accounts of Chem. Res., vol. 41 (2006) 1133-1142.

Moad et al., "Some recent developments in RAFT polymerization," ACS Symp. Ser., vol. 1100 (2012) 243-258.

Yandek et al., "Effects of Peripheral Architecture on the Properties of Aryl Polyhedral Oligomeric Silsesquioxanes," J. Phys. Chem. vol. 116, (2012) pp. 16755-16765.

Moore et al., "Increasing the solubility of inert peripherally aromatic poss," ACS Division of Polymer Chem Document No. 154:410824, citing Polym. Preprints, vol. 52 (2011).

Ramirez et al., "Functionalization of fluoroalkyl polyhedral oligomeric silsesquioxanes (F-POSS)," ACS Symp. Ser., vol. 1106 (2012) 95-109.

Ramirez et al., "Incompletely condensed fluorozlkyl silsesquioxanes and derivatives: precursors for low surface energy materials,"JACS, vol. 133 (2011) 20084-20087.

Stamenovic et al., "Norbornenyl-based RAFT agents for the preparation of functional polymers via thiol-ene chemistry," Macromol., vol. 44 (2011) 5619-5630.

Tan et al., "Tailoring micelle formation and gelation in (PEG-P(MA-POSS)) amphiphilic hybrid block copolymers," Macromol., vol. 44 (2011) 622-631.

Thomas et al., "Kinetics and molecular weight control of the polymerization of acrylamide via RAFT," Macromol., vol. 37 (2004) 8941-8950.

Tsujii et al., "Mechanism and kinetics of RAFT-mediated graft polymerization of styrene on a solid surface. 1. experimental evidence of surface radical migration," Macromol,. vol. 34 (2001) 8872-8878.

Wang et al., "Hepta(3,3,3-trifluoropropyl) polyhedral oligomeric silsesquioxane-capped poly(N-isopropylacrylamide) telechelics: synthesis and behavior of physical hydrogels," Appl. Mater. & Interf., vol. 3 (2011) 898-909.

Zeng et al., "Rapid deswelling and reswelling response of poly(N-isopropylacrylamide) hydrogels via formation of interpenetrating polymer networks with polyhedral olgiomeric silsesquioxane-capped poly(ehtylene oxide) amphiphilic telechelics," J. Phys. Chem. B., vol. 113 (2009) 11831-11840.

Zeng et al, "Organic-inorganic hybrid hydrogels involving poly(N-isopropylacrylamide) and polyhedral oligomeric silsesquioxane: preparation and rapid thermoresponsive properties," J. Polym. Sci. Part B Polym. Phys., vol. 47 (2009) 504-516.

Zeng et al., "Nanostructures and surface hydrophobicity of epoxy thermosets containing hepta(3,3,3-trifluorpropyl) polyhedral oligomeric silsesquioxane-capped poly(hydroxyether of bisphenol A) telechelics," J. Colloid Interf. Sci., vol. 363 (2011) 250-260.

Zhang et al., "Synthesis via RAFT polymerization of tadpole-shaped organic/inorganic hybrid poly(acrylic acid) containing polyhedral oligomeric silsesquioxane (POSS) and their self-assembly in water," Macromol., vol. 42 (2009) 2563-2569.

Brenier, "Bifunctional surfaces with superhydrophobic and plasmonic properties," J. Phys. Chem. C., vol. 115 (2011) 10544-10549.

Campos et al., "Fluoroalkyl-functionalized silica particles: synthesis, characterization, and wetting characteristics," Langmuir, vol. 27 (2011) 10206-10215.

Campos et al., "Superoleophobic surfaces through control of sprayed-on stochastic topography," Langmuir, vol. 28 (2012) 9834-9841.

Ogawa et al., "Development of a transparent and ultrahydrophobic glass plate," Jpn. J. Appl. Phys., vol. 32 (1993) L614-L615.

Sagiv et al., "Organized monolayers by adsorption. 1. formation and structure of oleophobic mixed monolayers on solid surfaces," JAGS, vol. 102 (1980) 92-98.

Roghani-Mamaquani et al., "In situ controlled radical polymerization: a review on synthesis of well-defined nanocomposites," Polym. Rev., vol. 52 (2012) 142-188.

Badrinarayanna et al., "Zirconium tungstate/cyanate ester nanocomposites with tailored thermal expansivity," Composites Sci and Tech., vol. 71 (2011) 1385-1391.

(56) References Cited

OTHER PUBLICATIONS

Cordes, "Recent developments in the chemistry of cubic polyhedral oligosilsesquioxanes," Chem. Rev., vol. 110 (2010) 2081-2173.
United States Patent and Trademark Office, Non-Final Office Action in U.S. Appl. No. 13/624,151, mailed Nov. 7, 2013, 12 pages total.
United States Patent and Trademark Office, Final Office Action in U.S. Appl. No. 13/624,151, mailed May 30, 2014, 11 pages total.
United States Patent and Trademark Office, Non-Final Office Action in U.S. Appl. No. 13/624,355, mailed Sep. 24, 2014, 7 pages total.
United States Patent and Trademark Office, Non-Final Office Action in U.S. Appl. No. 14/013,600, mailed Aug. 22, 2014, 6 pages total.
United States Patent and Trademark Office, Non-Final Office Action in U.S. Appl. No. 13/210,915, mailed Jun. 11, 2014, 6 pages total.
United States Patent and Trademark Office, Notice of Allowance in U.S. Appl. No. 13/210,915, mailed Nov. 12, 2014, 8 pages total.
Davis et al., "Polycyanurate networks from anethole dimers: synthesis and characterization," Polym. Chem., vol. 50 (2012) 4127-4136.
Hamerton et al., "Studies on a dicyanate containing four phenylene rings and polycyanurate blends. 2. Application of mathematical models to the catalysed polymerization process," Polymer., vol. 44 (2003) 4839-4852.
Hudson and Nelson, University Physics 2d ed. 754 (Saunders College Publishing: Philadelphia 1990), p. 754.
Zhao et al., "Autocatalystic curing kinetics of thermosetting polymers: a new model based on temperature dependent reaction orders," Polymer., vol. 51 (2010) 3814-3820.
Sean M. Ramirez, "Synthesis and Free Radical Polymerization of Fluorinated Polyhedral Oligomeric Silsesquioxane (F-POSS) Macromers: Precursors for Low Surface Energy Materials," Presentation to the Chemistry Department of the Air Force Academy, Colorado Springs, Colorado, Apr. 12, 2012.
Seurer et al., "Influences of POSS peripheral, architecture, and spacer group on phenylethynphthalimide reactions," Polymer Preprints, vol. 50 (2009) 820-821.

* cited by examiner

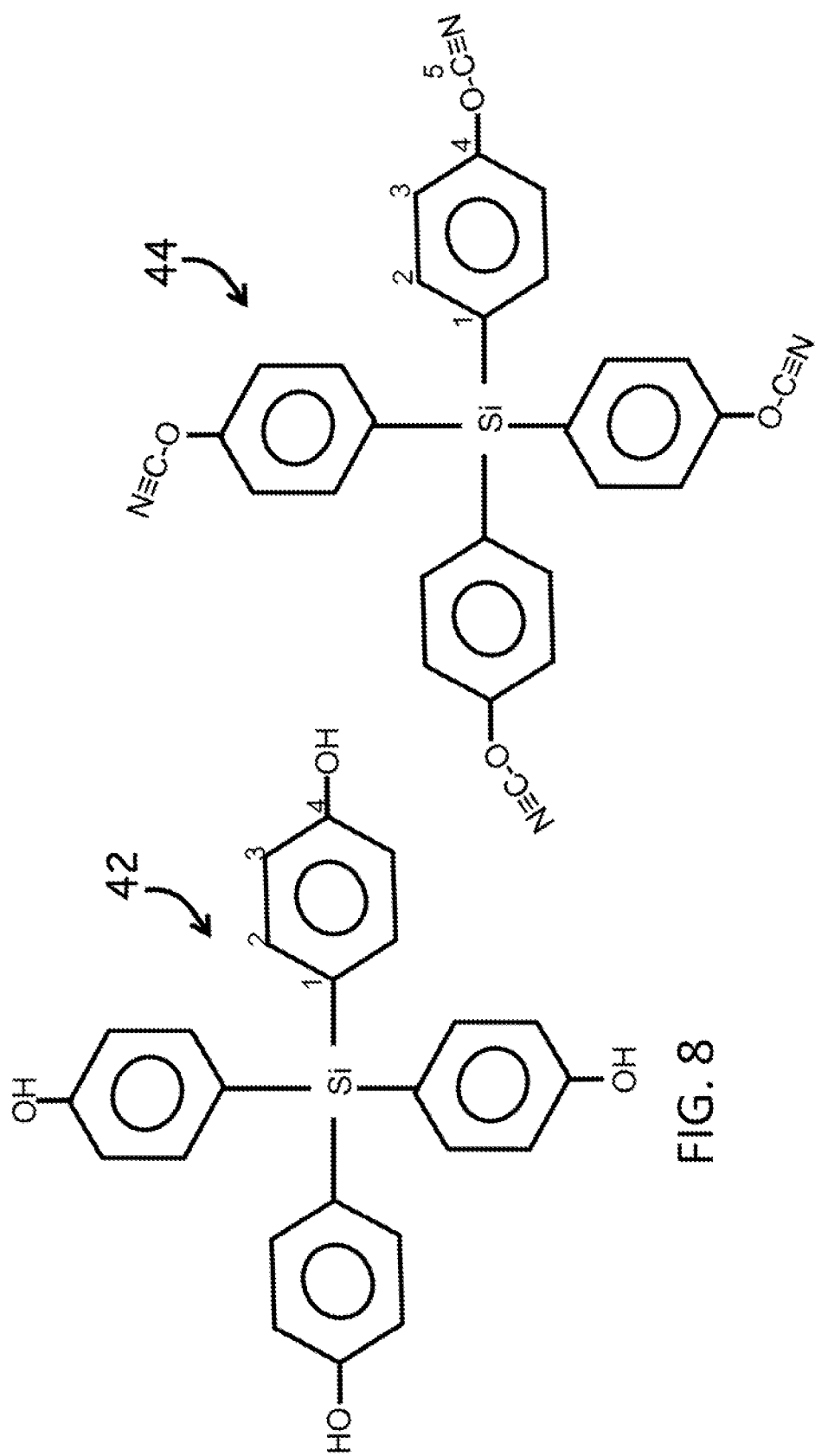

THERMOSETTING RESINS WITH ENHANCED CURE CHARACTERISTICS CONTAINING ORGANOFUNCTIONAL SILANE MOIETIES

RIGHTS OF THE GOVERNMENT

The invention described herein may be manufactured and used by or for the Government of the United States for all governmental purposes without the payment of any royalty.

FIELD OF THE INVENTION

The present invention relates generally to resins and, more particularly, to thermosetting resins.

BACKGROUND OF THE INVENTION

Thermosetting polymer materials are often used as adhesives and composite resins in applications that involve exposure to elevated temperatures. Therefore, there is an on-going need to improve thermo-chemical stability of cured resins in environments involving both elevated temperature and exposure to chemical agents (such as oxygen, water vapor, and acid vapor). This on-going need has given rise to a number of alternative materials that involve the cure of reactive groups such as cyanate esters, maleimides, benzoxazines, phthalonitriles, and aryl ethynyls. While these conventional resins are valued for their ease of use in affordable processes, such as resin transfer molding and filament winding, and for offering maximum service temperatures that are higher than those afforded by epoxy resins with similar processing characteristics, deficiencies remain.

For example, for conventional cyanate esters having more than about 3 mmol cyanurate per cubic centimeter, the fraction of uncured reactive groups is often larger than about 5% and, in fact, may be as much as 20%. These uncured reactive groups become detrimental to the performance of the thermoset polymer, e.g., unreactive cyanate esters may react with water at elevated temperatures to release carbon dioxide gas, which leads to blistering and mechanical failure of the resultant resin.

Some conventional approaches to combat the issues with uncured reactive groups has been to increase the final cure temperature and/or to increase catalyst level and activity; however, the former often requires temperatures exceeding 300° C., which impose significant added costs to many processing techniques while the latter is associated with decreased thermal stability in wet environments. Still another approach adds alkyl groups and thereby decreases the thermo-chemical and thermo-oxidative stability of the resin. In fact, the decreased thermo-chemical stability limits the maximum use temperature of such resins to values at least 50° C. lower than would otherwise be possible. Furthermore, the substantial molecular volume increase associated with such alkyl chains decreases the density of cross-linkages within a network segment and lowers the glass transition temperature of the resin.

There remains a need for high-temperature thermosetting resins having a glass transition temperature exceeding 280° C., with a flexible moiety having a high level of thermo-oxidative resistance, and which minimally adds to the molar volume of the network into which it is incorporated.

SUMMARY OF THE INVENTION

The present invention overcomes the foregoing problems and other shortcomings, drawbacks, and challenges of conventional thermosetting resins by providing high thermal stability and minimally-adding to the molar volume of the network in which it is incorporated. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a reactive, non-hydrolyzable silane includes a quaternary silicon atom and first and second terminal groups, each chemically bonded to the quaternary silicon atom. Both terminal groups include at least one reactive group that is selected from a group consisting of cyanate ester, epoxide, episulfide, acrylate, alkene, styrenic, maleimide, phthalonitrile, acetylene, aryl ethynylene, benzoxazine, anthracene, aniline, trifluorovinyl ether, and perfluorocyclobutyl.

In accordance with another embodiment of the present invention, a thermosetting resin includes a silane and a co-reactant monomer. The silane includes a quaternary silicon atom with first and second non-hydrolyzable moieties chemically bonded thereto. Each of the first and second non-hydrolyzable moieties includes respective first and second reactive groups. The reactive groups are selected from a group consisting of cyanate ester, epoxide, episulfide, acrylate, alkene, styrenic, maleimide, phthalonitrile, acetylene, aryl ethynylene, benzoxazine, anthracene, aniline, trifluorovinyl ether, and perfluorocyclobutyl.

Still another embodiment of the present invention is directed to a method, which includes substituting a silicon atom for at least one quaternary carbon atom having first and second non-hydrolyzable terminal groups. Each of the non-hydrolyzable terminal groups has at least one reactive group that is configured to form at least one network junction within a resin. Optionally, a linking group may be inserted between the silicon and the first non-hydrolyzable terminal group, the second non-hydrolyzable terminal group, or both.

An embodiment of the present invention is directed to a method that includes curing non-hydrolyzable silanes to form a resin. The non-hydrolyzable silanes include a quaternary silicon atom and first and second terminal groups that are chemically bonded to the quaternary atom. The first and second terminal groups each include at least one reactive group selected from the group consisting of cyanate ester, epoxide, episulfide, acrylate, alkene, styrenic, maleimide, phthalonitrile, acetylene, aryl ethynylene, benzoxazine, anthracene, aniline, trifluorovinyl ether, and perfluorocyclobutyl. These at least one reactive groups of the first and second terminal groups are configured to form more than 3 mmoles of network junctions per cubic centimeter volume of the resin.

According to yet another embodiment of the present invention, a thermosetting resin includes a plurality of non-hydrolyzable silanes, each having a quaternary silicon atom and four non-hydrolyzable groups chemically bonded thereto. Each non-hydrolyzable group includes a reactive group and is chemically bonded to the quaternary silicon atom. The reactive groups are configured to form at least one network junction within the thermosetting resin.

The above and other objects and advantages of the present invention shall be made apparent from the accompanying drawings and the descriptions thereof.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 8 illustrates a chemical structure for tetrakis(4-hydroxyphenyl)silane, a second intermediate in the synthesis of tetrakis(4-cyanatophenyl)silane according to the synthesis provided in FIG. 3.

FIG. 9 illustrates a chemical structure for tetrakis(4-cyanatophenyl)silane, a resin synthesized in accordance with one embodiment of the present invention.

DETAILED DESCRIPTION OF THE INVENTION

As used herein, "chemical structure" and "chemical formula" refer to symbolic products and processes involving symbolic manipulations of specific geometric arrangements of the representations or symbols of atoms of a symbolic molecule. Comparatively, "chemical synthesis," "chemical compound," and "chemical substance" refer to a physical process of manipulating atoms to form physically existing molecules and the physical products formed by these physical processes. Other general chemical terminology, such as "atom" and "reactive group" may be understood to refer to symbolic and physical entities, according to the context in which the terminology is used.

Figures 1, 2:
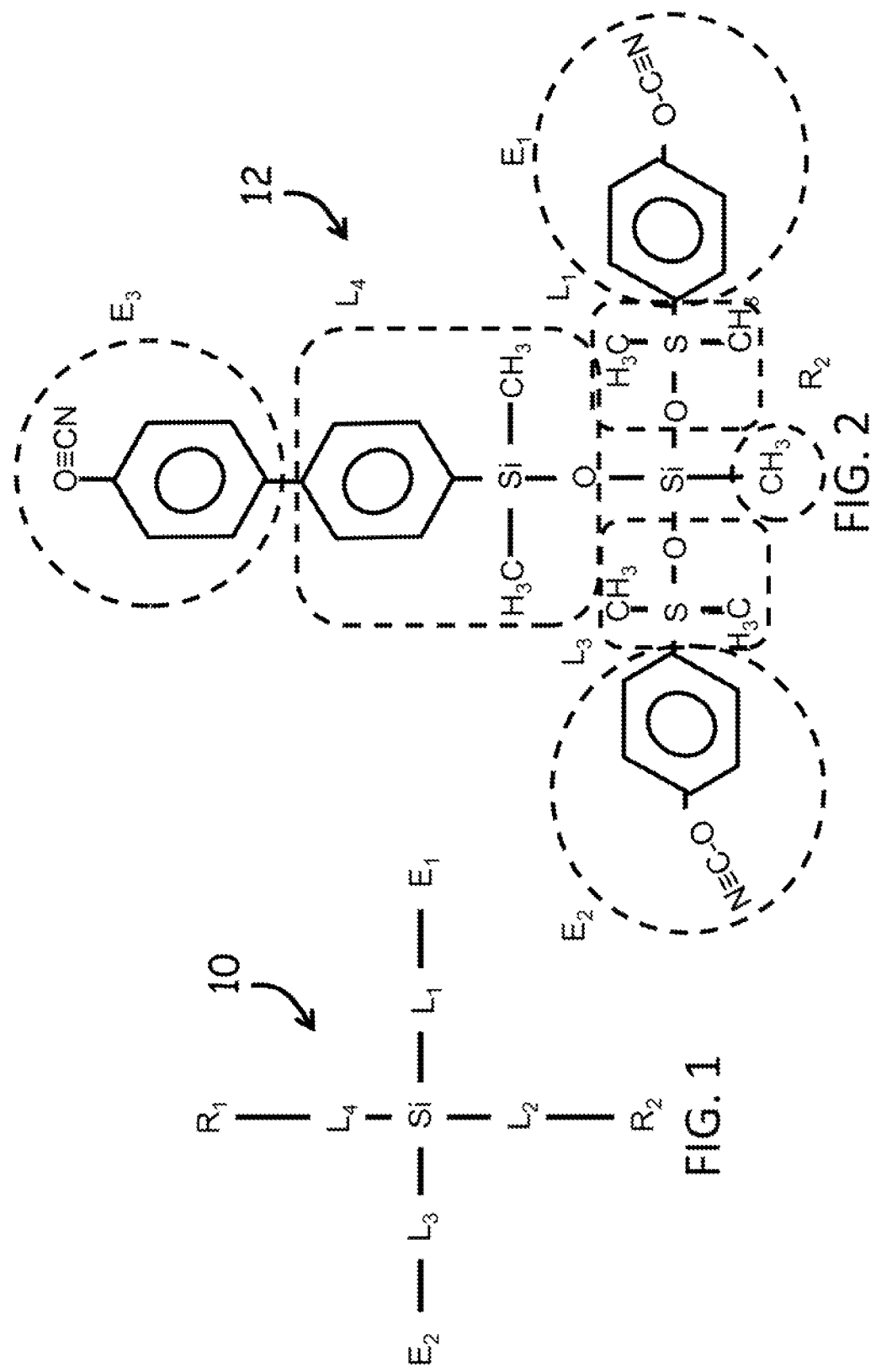
FIG. 1 illustrates a general, chemical formula for a reactive, non-hydrolyzable silane according to an embodiment of the present invention.
FIG. 2 illustrates a chemical structure for a reactive, non-hydrolyzable silane according to an embodiment of the present invention.

Turning now to the figures, and in particular to FIG. 1, a chemical formula for a reactive, non-hydrolyzable silane 10 is shown according to one embodiment. The illustrated non-hydrolyzable silane 10 includes first and second reactive terminal groups (or moieties) $E_1$, $E_2$, first and second non-reactive groups (or moieties) $R_1$, $R_2$, and a plurality of linking groups $L_1$, $L_2$, $L_3$, $L_4$, wherein the elements comprising the reactive terminal groups $E_1$, $E_2$, the non-reactive groups $R_1$, $R_2$, and the linking groups $L_1$, $L_2$, $L_3$, $L_4$ are selected from the group consisting of hydrogen (H), carbon (C), nitrogen (N), oxygen (O), fluorine (F), silicon (Si), phosphorus (P), sulfur (S), chlorine (Cl), bromine (Br), and iodine (I). The terminal and linking groups are selected to be non-hydrolyzable, e.g., Si—O—C bond sequences or Si—X bond sequences, wherein X is a halogen, are avoided. Instead, the terminal and linking groups $E_1$, $E_2$, $R_1$, $R_2$, $L_1$, $L_2$, $L_3$, $L_4$ are selected such that, when the resultant resin is fully cured, a resultant resin network (an extended macromolecular network of crosslinked silanes) includes more than 3 mmol of junctions per cubic center of resin network, wherein network junctions include chemical structures having three or more linkages to the resin network (not including any dangling terminal groups) connected by a central unit of at least one, and generally less than 8, atoms, excluding hydrogen.

While the illustrated non-hydrolyzable silane 10 is shown with two reactive terminal groups $E_1$, $E_2$, it should be readily apparent from those skilled artisans having the advantage of the disclosure provided herein, that silanes according to other embodiments of the present invention may comprise three or more reactive terminal groups and, optionally, one or more non-reactive terminal groups, one or more linking groups, or both. Moreover, the architecture of reactive and non-reactive terminal groups $E_1$, $E_2$, $R_1$, $R_2$ may be linear or branched. Reactive terminal groups $E_1$, $E_2$ may include one or more reactive functionalities as described in detail below. The linking groups $L_1$, $L_2$, $L_3$, $L_4$, if present, may be of any available architecture, including, for example, cyclic structures bridging the terminal groups $E_1$, $E_2$, $R_1$, $R_2$.

The one or more reactive functionalities (i.e., reactive groups) of the reactive terminal groups $E_1$, $E_2$ are configured to enable the formation of the resin network having the plurality of network junctions, which may comprise three or more arms. For example, the one or more functionalities may include cyanate esters, epoxides, episulfides, acrylates, alkenes, styrenics, maleimides, phthalonitriles, acetylenes, aryl ethynylenes, benzoxazines, anthracenes, anilines, trifluorovinyl ethers, and perfluorocyclobutyl. The network forming reaction may be initiated by heating (for example, to at least 70° C.), may occur in the presence of a catalyst, or both.

Selection of the non-reactive terminal groups $R_1$, $R_2$ is such that total molar volume is minimized. Also, the selected non-reactive terminal groups $R_1$, $R_2$ undergo less than about 5% weight loss when heated (rate of about 5° C./min in air) to temperatures of about 350° C. According to one embodiment of the present invention, and if two reactive terminal groups $E_1$, $E_2$ per silane 10 are present, the molar volume of the non-reactive terminal groups, $R_1+R_2$, is less than about 100 cc/mol, and, in some embodiments, is less than about 50 cc/mol. According to another embodiment of the present invention, and if three reactive terminal groups $E_1$, $E_2$, $E_3$ are present, the mole fraction of the non-reactive terminal group $R_1$ is less than 200 cc/mol. Suitable examples of non-reactive terminal groups $R_1+R_2$ may include, but are not limited to, methyls, phenyls, naphthyls, trimethylsilyls, trimethylsiloxies, and trifluoromethyls.

The linking groups $L_1$, $L_2$, $L_3$, $L_4$ (referenced generally herein as $L_n$, wherein n may any integer ranging from 0 to 4) are generally compact, may, in fact, be absent, generally will undergo less than about 5% weight loss when heated (rate of about 5° C./min in air) to temperatures of about 35° C. In embodiments of the present invention having two reactive terminal groups $E_1$, $E_2$, the combined molar volume of linking groups $L_n$ may be less than about 150 cc/mol; in embodiments of the present invention having more than two reactive terminal groups $E_1$, $E_2$, $E_3$ (and optionally $F_4$) the combined molar volume of the linking groups $L_n$ may be less than about 300 cc/mol. Suitable examples of linking groups $L_n$ may include, but are not limited to, dimethylsiloxies and methylenes.

FIG. 2 illustrates a silane 12 according to one exemplary embodiment of the present invention, wherein chemical structures for groups $E_1$, $E_2$, $L_1$, $L_2$, $L_3$, $L_4$, $R_1$, $R_2$ are designated as follows: $E_1$, $E_2$, and $E_3$ are aryl cynante esters ($E_3$ replacing $R_1$), $R_2$ is a methyl, $L_1$ and $L_3$ are dimethylsiloxanes, and $L_4$ is absent.

Reactive, non-hydrolyzable silanes 10 according to various embodiments of the present invention, and as compared to similar (or "analogous") compounds having the central silicon atom replaced by a carbon atom in a corresponding chemical formula (not shown), obtain higher conversions (percentage of silane monomer cured) according to a predetermined schedule of times and temperatures. Bond lengths between the central silicon atom and the adjacent atoms of the terminal or linking groups $E_1$, $E_2$, $L_1$, $L_2$, $L_3$, $L_4$, $R_1$, $R_2$ may range from about 180 pm to about 190 pm (analogous carbon-centered compound bond lengths range from about 140 pm to about 160 pm in length). Accordingly, an effective modulus of elastic deformation of bonds between the central silicon atom and adjacent atoms is generally lower than an effective modulus of elastic deformation of bonds between the central carbon atom and adjacent atoms in the analogous carbon-centered compound.

The lower elastic modulus afforded non-hydrolyzable silanes 10 according to embodiments of the present invention allows thermal fluctuations acting on the central silicon atom and its adjacent atoms to produce a greater range of thermal motions. Additionally, the longer bond lengths, as compared to the analogous carbon-centered compound, provide greater spacing between adjacent ones of the terminal and/or linking groups $E_1$, $E_2$, $L_1$, $L_2$, $L_3$, $L_4$, $R_1$, $R_2$. Altogether, the non-hydrolyzable silanes 10 according to embodiments of the present invention have an increased range of motion, which enables the groups $E_1$, $E_2$, $L_1$, $L_2$, $L_3$, $L_4$, $R_1$, $R_2$ to sample a greater range of geometric conformations at a given temperature. Because successful formation of network junctions often requires that the reactive groups exist within a narrow range of geometric conformations, the probability of reaching a geometric conformation suitable for network junction formation within a given length of time increases, as does the number of successful network junction formation events per unit time.

Relative rates of forward and reverse reactions in a reversible network-forming cross-linking reaction depend on a difference in energy between the cross-linked network (i.e., the product) and the initial, non-cross-linked monomers (i.e., the reactants) and in accordance with classical thermodynamic energy relationships. More specifically, the lower the energy of the product as compared to the energy of the reactants, the higher the relative rate of the forward reaction and, resultantly, the higher the concentration of products at equilibrium. The reverse also holds and results in a higher concentration of reactants. The energy level of the products and reactants includes, at least in part, an elastic energy component that depends on the geometric distortion (here, geometric distortion of the terminal or linking groups $E_1$, $E_2$, $L_1$, $L_2$, $L_3$, $L_4$, $R_1$, $R_2$). Geometric distortions tend to increase the internal elastic energy of the product and may be somewhat proportional to a modulus of elastic deformation adjoining adjacent atoms. Thus, reactants having bonds of lower moduli of elastic deformation reduces the energy associated with geometric distortion and minimizes the internal elastic energy of the network (product). As a result, the energy level of the network (product) relative to the non-cross-linked monomers (reactants) is lowered, and, resultantly, a higher concentration of cross-liked network relative to non-cross-linked monomer (i.e., a higher conversion level) may be realized.

Reactive, non-hydrolyzable silanes 10 according to various embodiments of the present invention also provide high densities of network junctions. Generally, a strong positive correlation exists between the number of network junctions (per unit volume) and key physical properties of resins, such as dry and wet glass transition temperatures.

However, the nature of these relationships depends on the specific architecture of the network junctions. For example, the network junction density of a resin cured by the cyclotrimerization of tricyanate esters featuring a single branch point in the monomer backbone serving as a network junction may be 3 mmol/cc, which corresponds to a dry glass transition temperature at full cure of at least 250° C. The network junction density of a cured dicyanate ester system having no branch points serving as network junctions once cyclotrimerization takes place may be at least 3 mmol/cc, which corresponds to a dry glass transition temperature at full cure of at least 280° C.

In those embodiments of the present invention wherein the central silicon atom is chemically bonded to three or four reactive groups $E_1$, $E_2$, $E_3$ (and optionally, $E_4$), there may be a minimal increase in volume and in thermo-oxidative stability as compared to the analogous carbon-centered compound. Other arrangements of flexible chemical bonds, such as propylene or cyclohexyl bridges may impart similar benefits but require a relatively greater volume, may decrease the dry glass transition temperature, and may reduce thermo-oxidative stability. Although improvements in thermo-oxidative stability and hydrophobicity are well-known attributes of silane functionality, the simultaneous cure enhancing capabilities represent an unexpected discovery.

Figure 3:
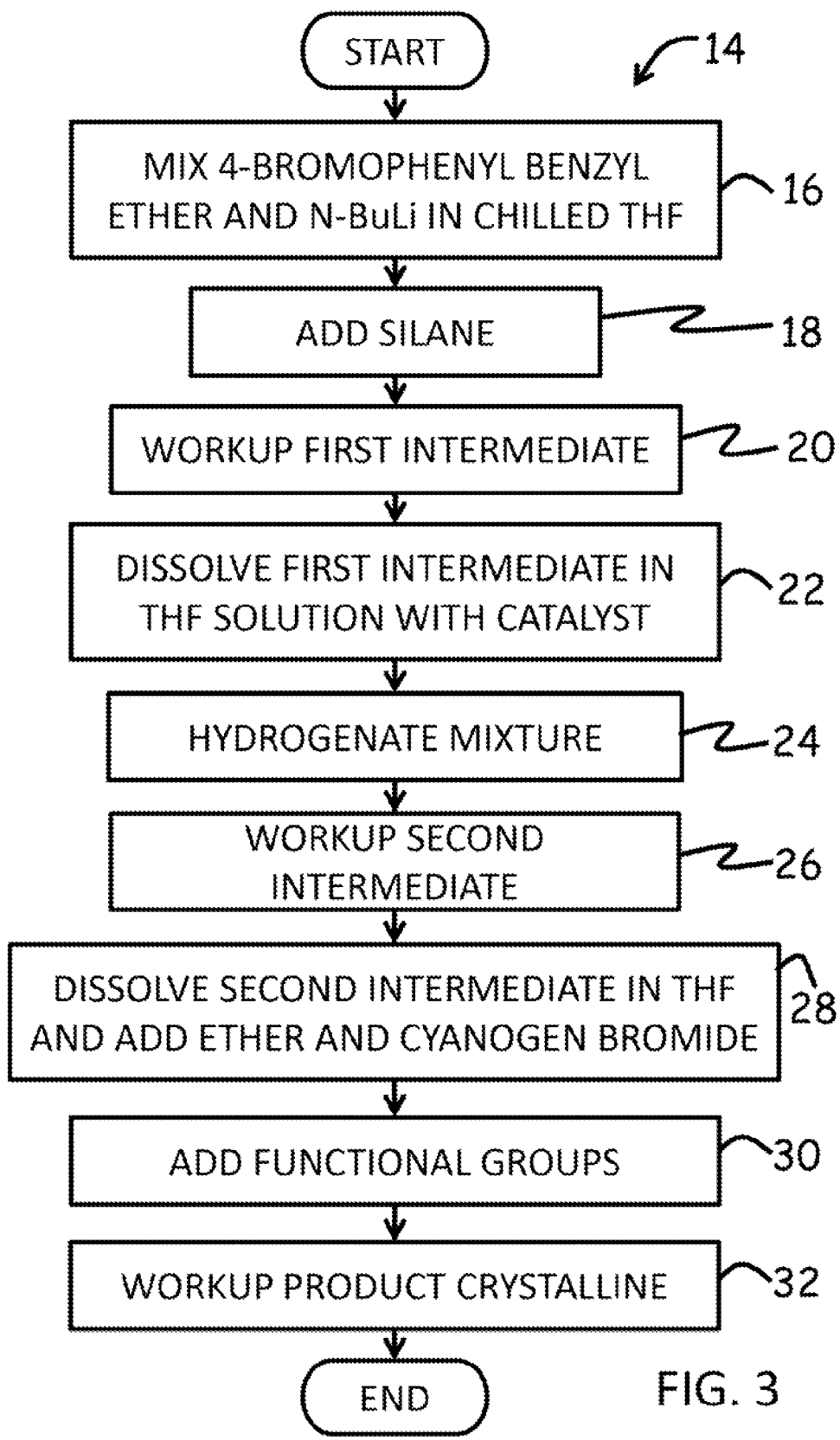
FIG. 3 is a flowchart illustrating a method of synthesizing reactive, non-hydrolyzable silanes according to an embodiment of the present invention.

With reference now to FIG. 3, a flowchart 14 illustrating a method of forming a reactive, non-hydrolyzable silane according to one embodiment of the present invention includes mixing equimolar parts of 4-bromophenyl benzyl ether and n-butyllithium (N-BuLi) in tetrahydrofuran, which is chilled to about −78° C. (Block 16). After the chilled mixture reacts, with stirring, the mixture is slowly treated with silane at a ratio of 1 mole silane to 3 moles n-butyllithium (Block 18). A first intermediate may be worked up (Block 20), by, for example, removing the cooling bath, removing solvents under pressure, and removing LiCl salt by the addition of chloroform. The first intermediate may also be precipitated into methanol and dried under nitrogen.

The first intermediate may be dissolved in a THF solution containing a catalyst, for example, palladium on carbon for hydrogenation (Block 22). Accordingly, the solution may be placed in a pressure safe vessel operably coupled to a hydrogenator and pressurized (Block 24). A second intermediate may be worked up (Block 26) which may include filtering out the catalyst and removing the solvent under reduced pressure. The second intermediate may also be purified by dissolution in THF, precipitated out in hexane, washed in ether, and dried under vacuum.

Reactive groups may be added to the silane (Block 30) by dissolving the second intermediate in a chilled ether solution of cyanogens bromide. The solution may be treated with triethylamine in a drop-wise manner, with diethyl ether, and filtered to remove hydrobromide salt. The organic layer may be washed with de-ionized water and a brine wash and dried over magnesium sulfate. A product crystalline may be worked up (Block 32) by precipitation out from ether.

Network-forming reaction of the product crystalline may be initiated by heat, for example, to at least 70° C. and may occur in the presence of a catalyst.

If desired, and as would be evident to those skilled in the art having the benefit of the disclosure provided herein, reactive, non-hydrolyzable silanes according to some embodiments of the present invention may further include additive material components. For example, and although not shown, reactive, non-hydrolyzable silanes may be co-reacted with other monomers lacking a central silicon atom so as to tailor the cure characteristics and other physical properties of the resulting resins. The co-reactant may be of the same type as the reactive, non-hydrolyzable silanes, although this is not required. Monomers of the co-reactant may react with other like monomers and not with the reactive, non-hydrolyzable silanes so as to form interpenetrating networks rather than co-polymerized networks. According to other embodiments, the monomers of the co-reactant may be at least partially reactive with the reactive, non-hydrolyzable silanes so as to form partly interpenetrating and partly co-polymerized networks.

For instance, according to one embodiment of the present invention, tris(4-cyanatophenyl)methylsilane may be co-polymerized with up to 10 wt % of an epoxy monomer (such as the diglycidyl ether of bisphenol A) to form a co-polymerized network. In other embodiments of the present invention, the epoxy monomer may be polymerized after being mixed with an equal weight of bis(4-phenylethynyl)phenyl ether, following which, the mixture may be gelled by reaction of the cyanate ester groups. On exposure to higher temperatures, entrapped phenylethynyl groups may undergo a separate cross-linking reaction to form an interpenetrating network.

Reactive, non-hydrolyzable silanes according to embodiments of the present invention may be used in systems containing insoluble filler particles and, more particularly, in systems containing dispersed nanoparticles, reinforcements, or other additives configured to impart mechanical, thermal, moisture-resistant, and/or electrical characteristics. Features of reactive, non-hydrolyzable silanes, as described herein, may remain largely unaltered by the addition of such materials so long as such materials do not interfere with surface organic reactive groups. The addition of filler particles may be useful, for example, as adhesives, sealants, composite resins, encapsulants, structures, and coatings.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

All manipulations of compounds and solvents were carried out using standard Schlenk line techniques. Tetrahydrofuran (THF), ether, chloroform, hexane, and toluene were dried by passage through columns of activated alumina under a nitrogen atmosphere and degassed prior to use. Anhydrous grade dichloromethane, acetone solvents, cyanogen bromide, n-butyllithium, and 10% palladium on carbon (wet, Degussa type) (Sigma-Aldrich Corp., St. Lois, Mo.) were used as received. Trichloromethylsilane and tetrachlorosilane (Gelest Inc., Morrisville, Pa.) and triethylamine (Sigma-Aldrich Corp.) were distilled prior to use. 4-benzyloxybromobenzene (Sigma-Aldrich Corp.) was recrystallized from ether prior to use.

Figure 4:
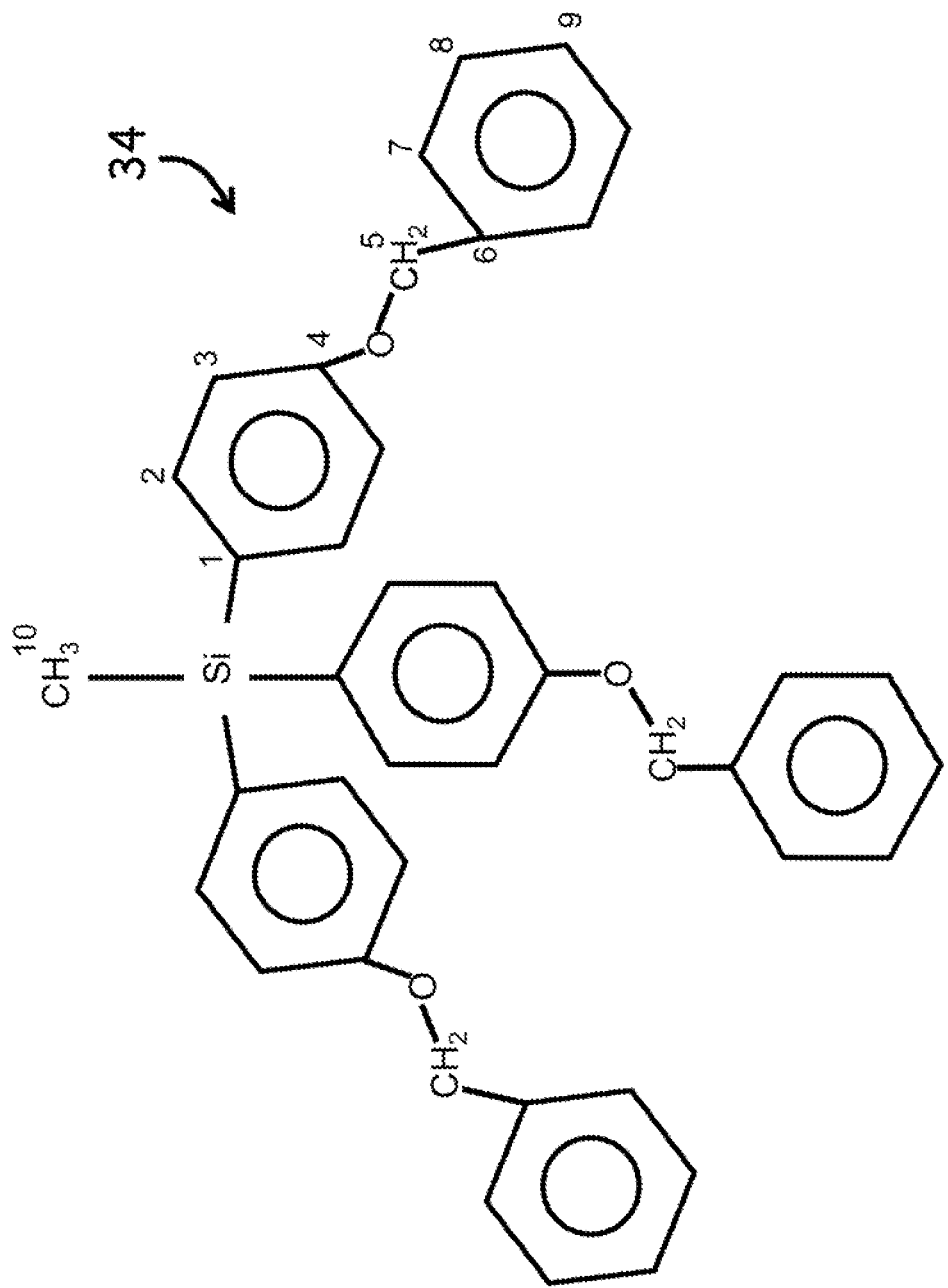
FIG. 4 illustrates a chemical structure for tris(4-benzyloxyphenyl)methylsilane, a first intermediate in the synthesis of tris(4-cyanatophenyl)methylsilane according to the synthesis provided in FIG. 3.

With reference now to FIG. 4, tris(4-benzyloxyphenyl) methylsilane 34 was prepared by chilling a solution of 400 mL THF and 4-bromophenyl benzyl ether (20.00 g, 76.0 mmol was treated with 2.5M n-BuLi (30.4 mLn, 76 mmol)) to −78° C. for 2 hr while stirring. The reacted solution, now heterogeneous, was treated with a slow addition of trichloromethylsilane (3.787 g, 25.33 mmol diluted with THF) and the cooling bath removed. The mixture reacted, while stirring and the solvents were removed under reduced pressure. Chloroform (300 mL) was added, the mixture stirred for an additional hour, and the mixture was filtered to remove LiCl salt. The solvent from the filtrate was removed under reduced pressure on a rotary evaporator. The off-white crude product was precipitated into methanol (400 mL), which was stirred overnight, filtered, and dried under nitrogen to afford tris(4-benzyloxyphenyl)methylsilane 34 as a white solid (13 g, 87% yield).

$^1H$, $^{13}C$, and $^{29}Si$ NMR measurements were performed on tris(4-benzyloxyphenyl)methylsilane 34 using a Bruker AC 300 or a Bruker 400 MHz instrument (Bruker Corp., Billerica, Mass.). $^1H$ and $^{13}C$ NMR chemical shifts are reported relative to the deuterated solvent peak ($^1H$, $^{13}C$: acetone-d6, δ 2.05 ppm, δ 29.9 ppm or CDCl$_3$, δ 7.28 ppm, δ 77.23 ppm). $^{29}Si$ NMR chemical shifts are reported relative to external tetramethylsilane at 0 ppm.

NMR assignments of the molecule shown in FIG. 4 include: $^1H$ NMR (acetone-d6) δ: 7.48 to 7.32 (m, 21H), 7.03 (d, J=8 Hz, 6H), 5.12 (s, 6H), 0.75 (s, 3H). $^{13}C$ NMR (acetone-d6) δ: 160.94 (C4), 138.32 (C6), 137.47 (C2), 129.35 (C8), 128.70 (C1, C9), 128.50 (C7), 115.38 (C3), 70.23 (C5), −2.66 (C10, SiCH$_3$). $^{29}Si$ NMR (acetone-d6) δ: −12.32 (s).

Figure 5:
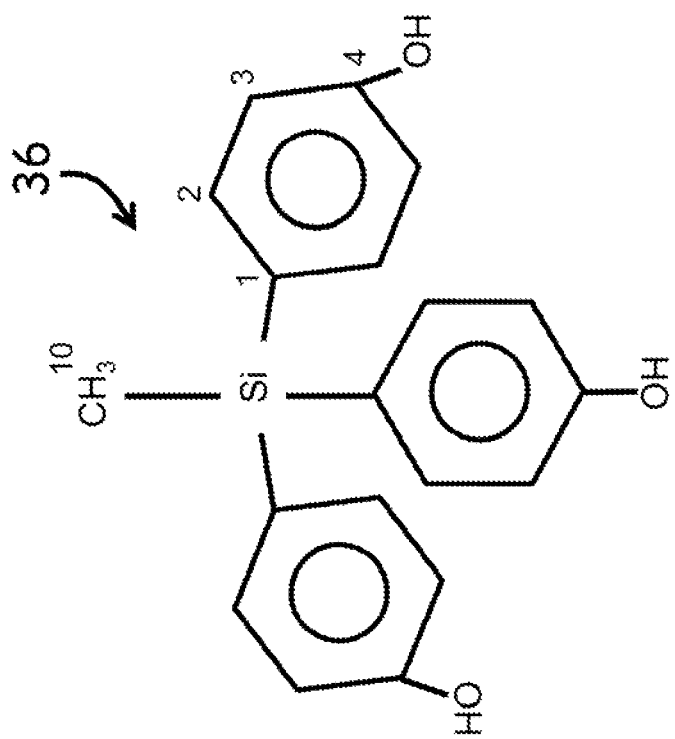
FIG. 5 illustrates a chemical structure for tris(4-hydroxyphenyl)methylsilane, a second intermediate in the synthesis of tris(4-cyanatophenyl)methylsilane according to the synthesis provided in FIG. 3.

A THF (200 mL) solution containing tris(4-benzyloxyphenyl)methylsilane 34 (10.00 g, 16.89 mmol) and 10 wt % palladium on carbon (400 mg) (e.g., the catalyst), was placed in a 1000 mL pressure safe vessel equipped with viton seals and, in turn, connected to a hydrogenator (Parr Instrument Co., Moline, Ill.). The vessel was pressurized with hydrogen (35 psi) and the solution was allowed to react with stirring for 48 hr. The catalyst was removed by filtration through celite, and the solvent was removed under reduced pressure to afford 4.60 g (85% yield) of tris(4-benzyloxyphenyl)methylsilane 36 (FIG. 5), as an off-white solid. For purification, tris(4-benzyloxyphenyl)methylsilane 36 was dissolved in THF and precipitated out in hexane. The white product was filtered, washed with ether, and dried under dynamic vacuum. NMR assignments of the molecule shown FIG. 5 include: $^1H$ NMR (acetone-d6) δ: 8.47 (s, 3H), 7.34 (d, J=8 Hz, 6H), 6.87 (d, J=8 Hz, 6H), 0.70 (s, 3H). $^{13}C$ NMR (acetone-d6) δ: 159.43 (C4), 137.52 (C2), 127.37 (C1), 115.92 (C3), −2.51 (C5, SiCH$_3$). $^{29}Si$ NMR (acetone-d6) δ: −12.57 (s).

Figure 6:
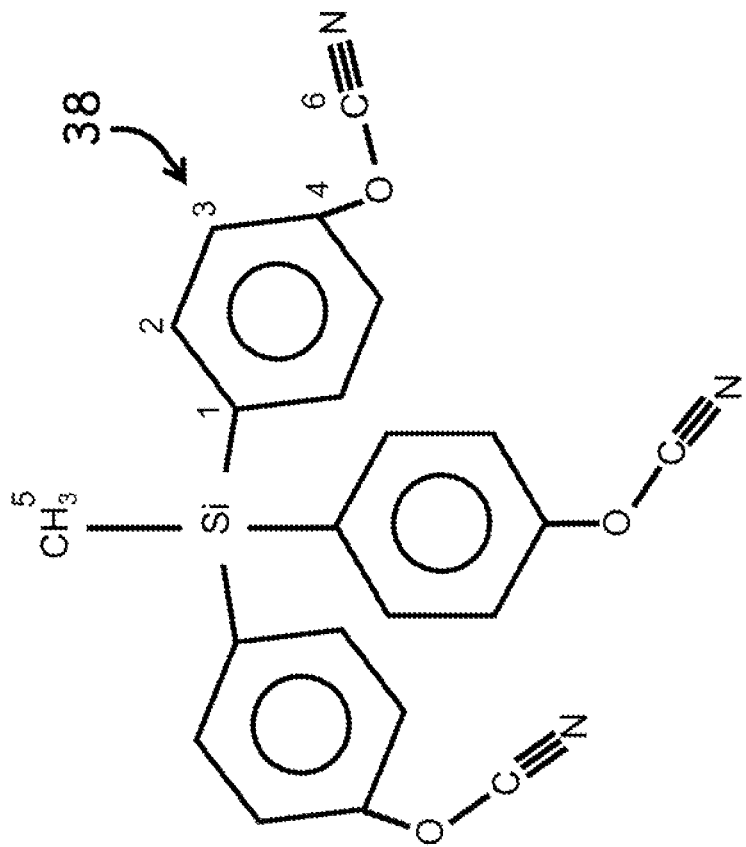
FIG. 6 illustrates a chemical structure for tris(4-cyanatophenyl)methylsilane, a resin synthesized in accordance with one embodiment of the present invention.

A chilled (−20° C.) ether (200 mL) solution containing tris(4-hydroxyphenyl)methylsilane, tris(4-benzyloxyphenyl) methylsilane 36 (FIG. 5) (4.0 g, 12.41 mmol), and cyanogen bromide (4.88 g, 46.53 mmol) in THF was treated with triethylamine (4.71 g, 46.53 mmol) in a drop-wise manner. The mixture was allowed to react for 2 hr with stirring at −20° C. Diethyl ether (500 mL) was added to the reaction mixture and stirred overnight. The mixture was filtered to remove the hydrobromide salt, and the organic layer was washed with (2×100 mL) de-ionized water, washed with a brine wash, and dried over MgSO$_4$. The solvents were removed under reduced pressure, and the crude product (3.2 g, 80% yield) was precipitated out from ether to afford 2.9 g (72%, yield) of tris(4-cyanatophenyl)methylsilane 38 (FIG. 6) as white a crystalline solid (mp 118° C., as determined on a Q2000 Differential Scanning Calorimeter (DSC) (TA Instruments, New Castle, Del.) under nitrogen flowing at 50 mL/min, with 5 minutes for equilibration at the maximum and minimum temperatures). NMR assignments of the molecule shown FIG. 6 include: $^1H$ NMR (acetone-d6) δ: 7.74 (d, J=9 Hz, 6H), 7.48 (d, J=9 Hz, 6H), 0.98 (s, 3H). $^{13}C$ NMR (acetone-d6) δ: 154.48 (C4), 137.37 (C2), 134.11 (C1), 115.13 (C3), 108.20 (C6, OCN), −4.43 (C5, SiCH$_3$). $^{29}Si$ NMR (acetone-d6) δ: −10.51 (s).

Elemental analyses were obtained from Atlantic Microlabs or performed on an EA2400 Series II combustion analyzer (PerkinElmer Inc., Waltham, Mass.). The combustion analysis for tris(4-cyanatophenyl)methylsilane 38 found a % C, 66.48 (66.01); % H, 3.80 (3.68); and % N 10.57 (10.68).

Using the estimates of molar volume provided by JOZEF BICERANO, *Prediction of Polymer Properties* (Marcel Dekker, 3d ed., 2002), the disclosure of which is incorporated herein by reference in its entirety, the molar volumes of the various portions of cured tris(4-cyanatophenyl)methylsilane 38 are determined as follows: central Si atom (28 cc/mol); methyl group (17 cc/mol), and phenyl cyanate ester (98 cc/mol). The central Si atom is expected to add just 23 cc/mol to the total network volume and rigid bonds connected to the terminal cyanate ester groups are replaced with more flexible bonds. Based on the Bicerano method, the density of cured tris(4-cyanatophenyl)methylsilane 38 is expected to be 1.17 g/cc, while that of the carbon analog is expected to be 1.21 g/cc.

In order to determine the density of cured tris(4-cyanatophenyl)methylsilane 38, the synthesized powder was melted, degassed at 150° C. for 30 minutes at 300 mm Hg, and poured into clean cylindrical silicone molds, which were preheated to 150° C. The cure cycle was about 1 hour at 150° C. followed by 24 hours at 210° C. under nitrogen. Ramp rates between the long dwells were about 5° C./min. The silicone molds were such that cylindrically-shaped disc specimens measuring 12 mm in diameter by 3 mm thick were produced.

The resultant specimens were good quality discs and free of voids. Discs of the cured cyanate ester were placed into a vessel with two solutions of $CaCl_2$ (dihydrate) in deionized water, at different known concentrations. The cured cyanate ester and dihydrate were combined until a neutrally buoyant solution was realized.

The density of the neutral solution was obtained by weighing a 10.00 mL volumetric flask containing the fluid. This value was compared to the expected density of a $CaCl_2$ solution at the known concentration and ambient conditions. The measured density was 1.25 g/cc. By comparison, the density of a carbon-containing analog, 1,1,1-tris(4-cyanatophenyl)ethane (commercially-available as ESR255), was determined to be 1.27 g/cc by the same method. These experimental values are about 5% higher than the theoretically-obtained value and, therefore, indicate that the molar volumes of the molecular components are likely to be about 5% smaller than calculated. While not bound by theory, such a discrepancy is believed to have a significant effect only on the estimated molar volume of the phenyl cyanate esters, with a value of 91 cc/mol best satisfying the experimental data for both compounds. Further, it is believed that the substitution of silicon adds about 18 cc/mol to the total volume of the network. The fully cured tris(4-cyanatophenyl)methylsilane 38 is expected to have about 3.15 mmol cyanurate per cubic centimeter volume of the resin, and because the tri-functional silicon atom also serves as a physical cross-link, about 6.3 mmol cross-links per cubic centimeter are expected to be present in the fully cured network. The expected, fully cured glass transition temperature of the network is above 300° C.

Example 2

Tetrakis(4-benzyloxyphenyl)silane 40 (FIG. 7) was prepared by chilling a solution of 400 mL THF and 4-bromophenyl benzyl ether (20.00 g, 76.0 mmol was treated with 2.5M n-BuLi (30.4 mL, 76 mmol)) to −78° C. for 2 hr while stirring. The reacted solution, now heterogeneous, was treated with a slow addition of tetrachlorolsilane (3.22 g, 19 mmol diluted with THF) and the cooling bath removed. The mixture was allowed to reflux at 550° C., with stirring, for two nights. The solvents were removed under reduced pressure. Chloroform (300 mL) was added, the mixture stirred for an additional hour, and the mixture was filtered to remove LiCl salt. The solvent from the filtrate was removed under reduced pressure on a rotary evaporator. The off-white crude product was precipitated into methanol (400 mL), which was stirred overnight, filtered, and dried under nitrogen to afford tetrakis(4-benzyloxyphenyl)silane 40 as a white solid (11 g, 76% yield).

$^1H$, $^{13}C$ and $^{29}Si$ NMR measurements were performed on the white solid product using the Bruker AC 300 or the Bruker 400 MHz instrument (Bruker Corp.). $^1H$ and $^{13}C$ NMR chemical shifts are reported relative to the deuterated solvent peak ($^1H$, $^{13}C$: acetone-d6, δ 2.05 ppm, δ 29.9 ppm or $CDCl_3$, δ 7.28 ppm, δ 77.23 ppm). $^{29}Si$ NMR chemical shifts are reported relative to external tetramethylsilane at 0 ppm.

Figure 7:
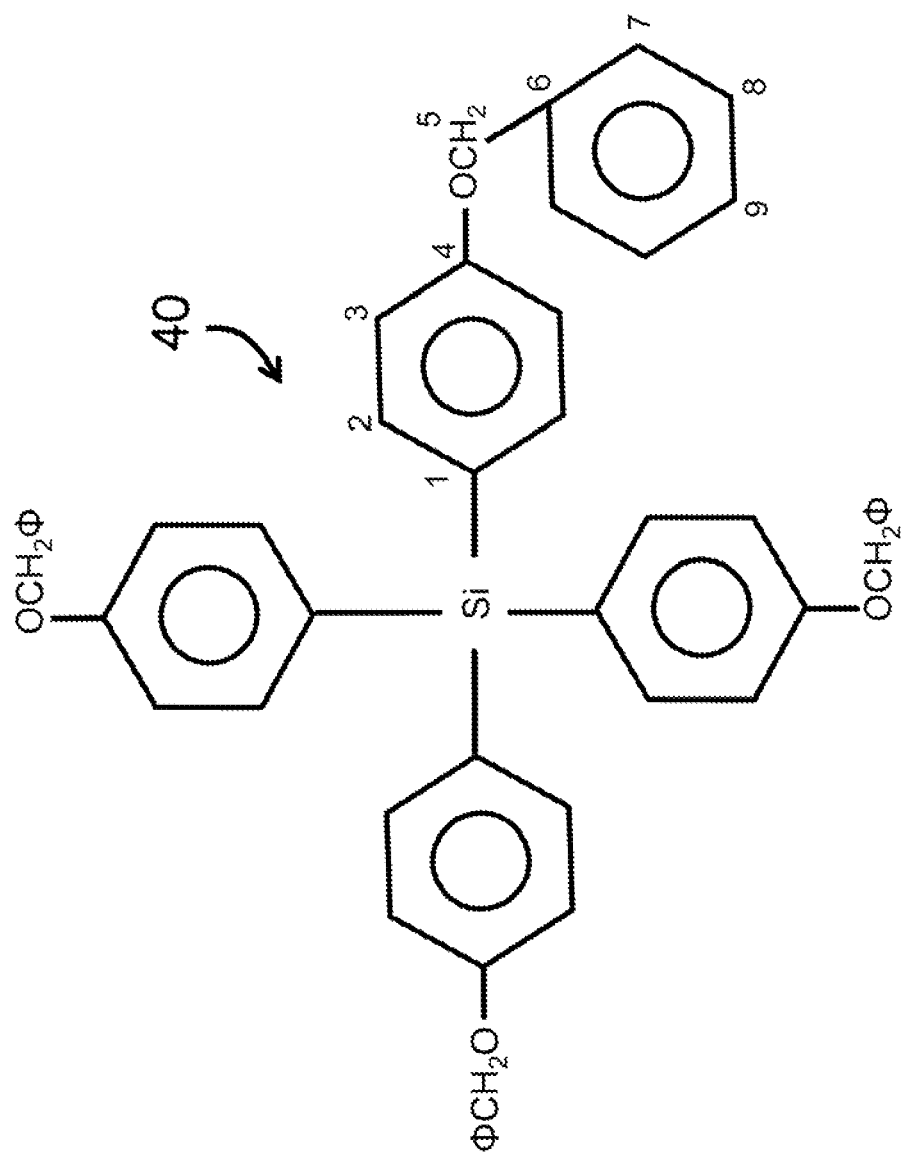
FIG. 7 illustrates a chemical structure for tetrakis(4-benzyloxyphenyl)silane, a first intermediate in the synthesis of tetrakis(4-cyanatophenyl)silane according to the synthesis provided in FIG. 3.

NMR assignments of tetrakis(4-benzyloxyphenyl)silane 40, as shown in FIG. 7, include: $^1H$ NMR ($CDCl_3$) δ: 7.54-7.38 (m, 28H), 7.05 (d, J=9 Hz, 8H), 5.12 (s, 8H). $^{13}C$ NMR (CDCl3) δ: 160.54 (C4), 137.84 (C2), 136.98 (C6), 128.66 (C8), 128.06 (C9), 127.59 (C7), 126.42 (C1), 114.46 (C3), 69.80 (C5). $^{29}Si$ NMR (CDCl3) δ: −14.60 (s)

A THF (200 mL) solution containing tetrakis(4-benzyloxyphenyl)silane 40 (10.00 g, 13.15 mmol) and 10 wt % palladium on carbon (400 mg) (e.g., catalyst), was placed in the 1000 mL pressure safe vessel equipped with viton seals and, in turn, connected to the hydrogenator, as provided above. The vessel was pressurized with hydrogen (35 psi) and the solution was allowed to react with stirring for 48 hr. The catalyst was removed by filtration through celite, and the solvent was removed under reduced pressure to afford 4.80 g (91% yield) of tetrakis(4-hydroxyphenyl)silane 42 (FIG. 8) as an off-white solid. For purification, tetrakis(4-hydroxyphenyl)silane 42 was dissolved in THF and precipitated out in hexane. The white product was filtered, washed with ether, and dried under dynamic vacuum. NMR assignments of the molecule shown in FIG. 8, include: $^1H$ NMR (acetone-d6) δ: 8.63 (s, 4H), 7.38 (d, J=6 Hz, 8H), 6.81 (d, J=6 Hz, 8H). $^{13}C$ NMR (acetone-d6) δ: 159.54 (C4), 138.59 (C2), 125.98 (C1), 115.92 (C3). $^{29}Si$ NMR (acetone-d6) δ: −14.64 (s).

A chilled (−20° C.) ether (200 mL) solution containing tetrakis(4-hydroxyphenyl)silane 42 (4.0 g, 10 mmol), and cyanogen bromide (5.22 g, 50 mmol) in THF was treated with triethylamine (5.06 g, 50 mmol) in a drop-wise manner. This mixture was allowed to react for 2 hr with stirring at −20° C. Dichloromethane (200 mL) was added to the reaction mixture and stirred for an hour. The mixture was filtered to remove the hydrobromide salt, and the organic layer was washed with (2×100 mL) DI water, washed with a brine wash, and dried over $MgSO_4$. The solvents were removed under reduced pressure, and crude product (3.8 g, 76% yield) was precipitated from ether to afford 3.5 g (72% yield) of tetrakis(4-cyanatophenyl)silane 44 (FIG. 9) as white crystalline solid (mp 169° C.). NMR assignments of tetrakis(4-cyanatophenyl)silane 44, as shown in FIG. 9, include: $^1H$ NMR (acetone-d6) δ: 7.77 (d, J=8, 8H), 7.54 (d, J=8, 8H). $^{13}C$ NMR (acetone-d6) δ: 155.73 (C4), 139.72 (C2), 132.38 (C1), 116.40 (C3), 109.02 (C5, OCN). $^{29}Si$ NMR (acetone-d6) δ: −14.95 (s).

Using the estimates of molar volume provided by Bicerano, as in the previous example, the molar volumes of the various portions of cured tris(4-cyanatophenyl)methylsilane 44 may be determined as follows: central Si atom (28 cc/mol) and phenyl cyanate ester (98 cc/mol). The central Si atom is expected to add just 23 cc/mol to the total network volume and four rigid bonds connected to the terminal cyanate ester groups are replaced with more flexible bonds. Based on the Bicerano method, the density of cured tetrakis(4-cyanatophenyl)silane 44 is expected to be 1.22 g/cc, while that of the carbon analog is expected to be 1.25 g/cc. The fully cured density of Primaset® LECy (a commercially-available analog, Lonza Group Ltd., Basel, Switzerland) is 1.23 g/cc.

Therefore, co-cured blends of tetrakis(4-cyanatophenyl)silane 44 with Primaset® LECy may be expected to have a very similar density.

In order to determine the density of cured tetrakis(4-cyanatophenyl)silane 44, equal weights of tetrakis(4-cyanatophenyl)silane 44 and Primaset® LECy, were combine, melted, and degassed at 150° C. for 30 minutes at 300 mm Hg. Blending tetrakis(4-cyanatophenyl)silane 44 with Primasaet® LECy lowered the melting point (i.e., the melting point of the pure tetrakis(4-cyanatophenyl)silane 44 was too high to afford a reasonable level of processability as a single-component resin). The samples were poured into clean cylindrical silicone molds preheated to 150° C. The co-cure cycle was about 1 hour at 150° C. followed by 24 hours at 210° C. under nitrogen. Ramp rates between the long dwells were about 5° C./min. The silicone molds were such that cylindrically-shaped disc specimens measuring 12 mm in diameter by 3 mm thick were produced.

The resultant specimens were good quality discs and free of voids. Discs of the co-cured cyanate ester were placed into a vessel and two solutions of CaClz (dihydrate) in deionized water, at different known concentrations. The cured cyanate ester and dehydrate were combined until a neutrally buoyant solution was realized.

The density of the neutral solution was obtained in the manner described above in Example 1. The measured density obtained by this method was 1.26 g/cc. When the density of LECy is taken into consideration, the projected density of the pure cured tetrakis(4-cyanatophenyl)silane 44 would be 1.29 g/cc. As in Example 1, the experimental value was about 5% higher than the theoretically-obtained value and is consistent with a value of 90 cc/mol for the molar volume of an aryl cyanate ester. While not bound by theory, it is believed that the substitution of silicon adds less than 20 cc/mol to the total volume of the network, even though a direct experimental comparison was not made. The fully cured tris(4-cyanatophenyl)methylsilane 44 was expected to have about 3.4 mmol cyanurate per cubic centimeter, and because the tetra-functional silicon atom also serves as a network junction upon cure, about 6.0 mmol network junctions per cubic centimeter are expected to be present in the fully cured network. For the co-network, the calculated number of cyanurates and network junctions were 3.25 mmol/cc and 4.5 mmol/cc, respectively. The fully cured glass transition temperature for both the pure cured tetrakis(4-cyanatophenyl)silane 44 as well as its co-network with an equal weight of fully cured Primaset® LECy tetrakis(4-cyanatophenyl)silane 44 are therefore expected to be well above 300° C.

Example 3

The dry glass transition temperature for partially- or fully-cured cyanate ester resins is related to the extent of cure through the diBenedetto equation:

$$\frac{T_G - T_{G0}}{T_{G\infty} T_{G0}} = \frac{\lambda a}{1 - (1 - \lambda)a},$$

which is a monotonic, one-to-one function describing this relationship quantitatively, and wherein $T_G$, $T_{G0}$, and $T_{G\infty}$ represent the glass transition temperatures of the partially-cured polymer, monomer, and fully-cured networks, respectively. The conversion factor, $\alpha$, represents the fraction of monomer groups that have reactive, and $\lambda$ is an adjustable parameter that typically takes on values ranging from about 0.25 to about 0.45 for cyanate esters.

As a result, and for a given cyanate ester, the higher dry glass transition temperature may be a reliable indication of a higher degree of cure. Moreover, if the glass transition temperatures of uncured monomer and fully cured resin are available, the use of the diBenedetto equation may provide reliable approximations of the relative degree of cure when comparing multiple resin systems on the basis of as-cured dry glass transition temperature values. In fact, even when a complete set of parameters for the diBenedetto equation is not known, the physical mechanisms underlying the equation provide strong constraints on the unknown parameters and, thus, reliable approximations the extent of cure, may still be possible.

Cured resin samples were prepared by either melting the tris(4-cyanatophenyl)methylsilane 38 (FIG. 6) powder (Example 1) and/or mixing the tetrakis(4-cyanatophenyl)silane 44 (FIG. 9) powder (Example 2) with Primaset® LECy liquid and melting the mixture at 150° C. under a reduced pressure of 300 mm Hg for 30 minutes. The heated mixture was poured into a reinforced silicone casting mold (12 mm diameter×3 mm discs) and cured by heating in an oven under nitrogen to 150° C. for 1 hour, 210° C. for 24 hours, and 150° C. prior to de-molding. Heating ramps were 5° C./min.

Thermomechanical analysis of cured samples was performed using a TA Q400 thermomechanical analyzer (TMA) (TA Instruments) in dynamic (oscillatory compression) TMA mode. Heating and cooling rates of 50° C./min were used, and a program of heating to 350° C., cooling to 100° C., and re-heating to 350° C. (450° C. for the control sample ESR255) was used. A standard thermal cycling procedure, using limits of 0° C. and 200° C., was used to determine and correct for the thermal lag caused by rapid heating rates. The mean compressive load on the samples was 0.1 N, with an oscillatory force applied at an amplitude of 0.1 N at a frequency of 0.05 Hz.

Thermogravimetric analysis (TGA) was carried out using a TA Q5000 under 60 mL/min of either nitrogen or air (TA Instruments). For TGA analysis, about 2 mg chips of the cured discs were heated at 10° C./min. to 600° C. Differential scanning calorimetry (DSC) was performed using a TA Q200 DSC (TA Instruments) while heating about 5 mg of uncured resin from room temperature to 350° C., cooling to 100° C., and re-heating to 350° C., all at 10° C. per minute for tetra(4-cyanatophenyl)silane 44 (FIG. 9). For tris(4-cyanatophenyl)methylsilane 38 (FIG. 6) and its carbon-containing analog, ESR255, the DSC scans involved heating and cooling at 10° C./min to room temperature, heating to 120° C., cooling to −90° C., heating to 350° C., cooling to 100° C., and heating again to 350° C., in sequence, so as to estimate the sub-ambient glass transition temperature of the uncured resin.

To estimate the heat capacity ratio factor in the diBenedetto equation for ESR255, the DSC program involved heating at 10° C./min to 200° C., holding for 5 min at 200° C., cooling at 10° C./min to 0° C., re-heating at 10° C./min to 350° C. This method causes partial cure of the sample and allows the DSC to measure the glass transition temperature and the extent of cure of the partially cured sample. The glass transition temperature, combined with the uncured and fully cured glass transition temperatures, enables experimental determination of the ratio.

Table 1 (below) provides the results of the DSC, TGA, and TMA experiments and the derived diBenedetto parameters for the compounds tris(4-cyanatophenyl)methylsilane 38 (FIG. 6), tetrakis(4-cyanatophenyl)silane 44 (FIG. 9) and Primaset® LECy in equal proportions, and ESR255, i.e., 1,1,1-tris(4-cyanatophenyl)ethane, which is the to tris(4-cyanatophenyl)methylsilane 38 carbon analog.

In the DSC experiment, a glass transition temperature of 123° C. was determined for ESR255 that had a residual enthalpy of cure of 351 J/g lower than the uncured sample (which showed 504 J/g enthalpy of cure using the same baseline). Because full cure at 350° C. was not necessarily obtained, the standard enthalpy of cure for cyanate esters (100 kJ/eq, or 866 J/g) was used to estimate conversion from the decrease in residual enthalpy rather than the residual enthalpy itself. The resultant conversion was 41%, and the resultant value of the heat capacity ratio, often abbreviated as λ, was 0.38. For cyanate esters, in general, a reasonable range for values of this parameter is 0.25 to 0.45.

As to ESR255, the data was sufficient to estimate the value of conversion with confidence; however, for the other resins, only a range could be estimated from the following facts: the uncured glass transition of cyanate esters generally ranges from at least −50° C. to about 50° C.; the effect of silicon substitution is to lower the glass transition temperature of a fully cured resin by at least 40° C.; a lower glass transition temperature is accompanied by a corresponding increase in the coefficient of thermal expansion (from Table 1, both tris (4-cyanatophenyl)methylsilane 38 (FIG. 6) and tetrakis(4-cyanatophenyl)silane 44 (FIG. 9) exhibit a higher coefficient of thermal expansion than ESR255); and values for the diBenedetto parameter, λ, fall within the range 0.25-0.45 for analogous cyanate esters. Based on the relative coefficients of thermal expansion and the data for analogous compounds, as well as the reported glass transition temperature of Primaset® LECy at full cure, the glass transition temperature of tris(4-cyanatophenyl)methylsilane 38 (FIG. 6) and tetrakis(4-cyanatophenyl)silane 44 (FIG. 9) would reasonably be expected to be lower than that of ESR255. A minimum estimate of conversion was obtained using the maximum values for uncured glass transition temperature, fully cured glass transition temperature, and λ.

TABLE 1

| Resin | $T_G$ (DSC, uncured) | $T_G$ (TMA, as-cured) | $T_G$ (TMA, fully cured) | CTE (TMA, cured to 350° C.) | Conversion (as-cured) |
| --- | --- | --- | --- | --- | --- |
| tris(4-cyanatophenyl)methylsilane | −6° C. | >350° C. | >350° C. | 56 | 92%-100% |
| tetrakis(4-cyanatophenyl)silane/ LECy 50/50 | <0° C. | >350° C. | >350° C. | 56 | 92%-100% |
| ESR255 | 6° C. | 302° C. | 419° C. | 48 | 86% |

Conversions for tris(4-cyanatophenyl)methylsilane 38 (FIG. 6) and tetrakis(4-cyanatophenyl)silane 44 (FIG. 9) assume an uncured $T_G$ of not more than −50° C. for the tetrakis(4-cyanatophenyl)silane 38 and, consequently, not more than 0° C. for a 50/50 mixture with Primaset® LECy. The fully cured $T_G$ is no more than 419° C., and the heat capacity ratio (1) in the diBenedetto equation ranges from about 0.25 to about 0.45.

According to the data in Table 1, the conversion obtained under identical cure conditions was higher for the silicon-containing compounds than for the carbon-containing analog. Hence, substitution of silicon did result in improvements to processing because the failure to attain high conversions without recourse to temperatures well in excess of 250° C. is a known limitation of rigid cyanate esters, such as Primaset® PT-30, that feature good thermo-oxidative stability. In the case of the silicon-containing materials, TGA measurements showed that the 5% decomposition temperatures were 403° C. under nitrogen and 400° C. in air for tris(4-cyanatophenyl)methylsilane 38 (FIG. 6) and 408° C. under nitrogen and 400° C. in air for tetrakis(4-cyanatophenyl)silane 44 (FIG. 9). Both resins retain adequate thermo-oxidative stability. At higher temperatures, the presence of silicon enables the formation of silicon dioxide, which may play a further protective role. As expected, the glass transition temperature values were all well in excess of 300° C.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A reactive, non-hydrolyzable silane comprising:
    a quaternary silicon atom;
    a first terminal group chemically bonded to the quaternary silicon atom;
    a second terminal group chemically bonded to the quaternary silicon atom, and
    a third terminal group chemically bonded to the quaternary silicon atom,
    wherein each of the first terminal group, the second terminal group, and the third terminal group include at least one reactive group comprising a triple bond that is selected from the group consisting of a cyanate ester and a phthalonitrile.

2. The reactive, non-hydrolyzable silane of claim 1, further comprising:
    at least one linking group between the quaternary silicon atom and the first terminal group, the second terminal group, the third terminal group, or two or more thereof.

3. The reactive, non-hydrolyzable silane of claim 2, wherein the at least one linking group comprises dimethylsiloxy or methylene.

4. The reactive non-hydrolyzable silane of claim 1, wherein the at least one reactive group comprising the triple bond is the cyanate ester.

5. The reactive, non-hydrolyzable silane of claim 1, further comprising:
    a fourth terminal group chemically bonded to the quaternary silicon atom,
    wherein the fourth terminal group includes at least one reactive group comprising a triple bond that is selected from the group consisting of the cyanate ester, the phthalonitrile, the acetylene, and the aryl ethynylene.

6. The reactive, non-hydrolyzable silane of claim 5, further comprising:
   at least one linking group between the quaternary silicon atom and the fourth terminal group.

7. The reactive, non-hydrolyzable silane of claim 6, wherein the at least one linking group comprises dimethylsiloxy or methylene.

8. The reactive, non-hydrolyzable silane of claim 5, wherein the first, second, third, and fourth terminal groups are each the cyanate ester.

9. The reactive, non-hydrolyzable silane of claim 8, wherein the silane has a chemical name of tetrakis(4-cyanatophenyl)silane.

10. The reactive, non-hydrolyzable silane of claim 1, further comprising:
    a fourth terminal group chemically bonded to the quaternary silicon atom, wherein the fourth terminal group is chemically inert.

11. The reactive, non-hydrolyzable silane of claim 10, wherein the fourth terminal group is selected from a group consisting of methyl, phenyl, naphthyl, trimethylsilyl, trimethylsiloxy, and trifluoromethyl.

12. The reactive, non-hydrolyzable silane of claim 10, further comprising:
    at least one linking group between the quaternary silicon atom and the first terminal group, the second terminal group, the third terminal group, or two or more thereof.

13. The reactive, non-hydrolyzable silane of claim 12, wherein the at least one linking group comprises dimethylsiloxy or methylene.

14. The reactive, non-hydrolyzable silane of claim 11, wherein the fourth terminal group is methyl, and wherein the silane has a chemical name of tris(4-cyanatophenyl)methylsilane.

* * * * *